(12) United States Patent
Stomp et al.

(10) Patent No.: US 6,815,184 B2
(45) Date of Patent: Nov. 9, 2004

(54) EXPRESSION OF BIOLOGICALLY ACTIVE POLYPEPTIDE IN DUCKWEED

(75) Inventors: Anne-Marie Stomp, Moncure, NC (US); Lynn Dickey, Cary, NC (US); John Gasdaska, Carrboro, NC (US)

(73) Assignee: Biolex, Inc., Pittsboro, NC (US)

( * ) Notice: Subject to any disclaimer, the term of this patent is extended or adjusted under 35 U.S.C. 154(b) by 123 days.

(21) Appl. No.: 09/915,873

(22) Filed: Jul. 26, 2001

(65) Prior Publication Data

US 2002/0088027 A1 Jul. 4, 2002

Related U.S. Application Data (60) Provisional application No. 60/221,705, filed on Jul. 31, 2000, and provisional application No. 60/293,330, filed on May 23, 2001.

(51) Int. Cl.[7] .................. C12P 21/04; C12N 5/10; C12N 5/11; A01H 1/00; A01H 9/00
(52) U.S. Cl. .............. 435/69.51; 435/320.1; 435/419; 800/288; 800/295; 536/23.1
(58) Field of Search ............. 536/23.1; 435/69.51, 435/320.1, 419; 800/288, 295, 278, 294

(56) References Cited

U.S. PATENT DOCUMENTS

| | | |
|---|---|---|
| 4,956,282 A | 9/1990 | Goodman et al. |
| 5,629,175 A | 5/1997 | Goodman et al. |
| 5,850,032 A | 12/1998 | Wann |
| 5,994,628 A | 11/1999 | Rodriguez |
| 6,020,169 A | 2/2000 | Lee et al. |
| 6,040,498 A | 3/2000 | Stomp et al. |
| 6,066,781 A | 5/2000 | Sutliff et al. |
| 6,096,546 A | 8/2000 | Raskin |
| 6,096,547 A | 8/2000 | Goodman et al. |

FOREIGN PATENT DOCUMENTS

| | | |
|---|---|---|
| EP | 0 141 484 A2 | 5/1985 |
| WO | WO 94/21796 A2 | 9/1994 |
| WO | WO 98/36085 A1 | 8/1998 |
| WO | WO 99/07210 A1 * | 2/1999 |
| WO | WO 99/19497 A1 | 4/1999 |
| WO | WO 99/47678 A2 | 9/1999 |

OTHER PUBLICATIONS

Murray, E. E. et al., "Codon Usage Plant Genes," *Nucleic Acids Research*, Jan. 25, 1989, pp. 477–498, vol. 17, No. 2.

* cited by examiner

*Primary Examiner*—Elizabeth F. McElwain
*Assistant Examiner*—Georgia L. Helmer
(74) *Attorney, Agent, or Firm*—Alston & Bird LLP (57) ABSTRACT

Methods, nucleic acid sequences, and transformed duckweed plant or duckweed nodule cultures for the expression and the secretion of biologically active polypeptides from genetically engineered duckweed are provided. Expression of recombinant polypeptides in duckweed is improved by modifying the nucleotide sequence of the expression cassette encoding the polypeptide for improved expression in duckweed. Recovery of biologically active polypeptides from duckweed is improved by linking the biologically active polypeptide to a signal peptide that directs the secretion of the polypeptide into the culture medium.

17 Claims, 2 Drawing Sheets

SEQUENCE LISTING

```
<160> NUMBER OF SEQ ID NOS: 12

<210> SEQ ID NO 1
<211> LENGTH: 554
<212> TYPE: DNA
<213> ORGANISM: Zea mays

<400> SEQUENCE: 1
gatcaagtgc aaaggtccgc cttgtttctc ctctgtctct tgatctgact aatcttggtt     60
tatgattcgt tgagtaattt tggggaaagc ttcgtccaca gttttttttt cgatgaacag    120
tgccgcagtg gcgctgatct tgtatgctat cctgcaatcg tggtgaactt atgtcttta    180 tatccttcac taccatgaaa agactagtaa tctttctcga tgtaacatcg tccagcactg    240
ctattaccgt gtggtccatc cgacagtctg gctgaacaca tcatacgata ttgagcaaag    300
atctatcttc cctgttcttt aatgaaagac gtcattttca tcagtatgat ctaagaatgt    360
tgcaacttgc aaggaggcgt ttctttcttt gaatttaact aactcgttga gtggccctgt    420
ttctcggacg taaggccttt gctgctccac acatgtccat tcgaatttta ccgtgtttag    480
caagggcgaa aagtttgcat cttgatgatt tagcttgact atgcgattgc tttcctggac    540
ccgtgcagct gcgg                                                      554

<210> SEQ ID NO 2
<211> LENGTH: 498
<212> TYPE: DNA
<213> ORGANISM: Artificial Sequence
<220> FEATURE:
<223> OTHER INFORMATION: Duckweed codon optimized nucleotide
      sequence encoding human alpha-2B interferon
<220> FEATURE:
<221> NAME/KEY: CDS
<222> LOCATION: (1)...(498)

<400> SEQUENCE: 2 tgc gac ctc ccc cag acc cac agc ctc ggg tcc cgc cgc acc ctc atg      48
Cys Asp Leu Pro Gln Thr His Ser Leu Gly Ser Arg Arg Thr Leu Met
 1               5                  10                  15 ctg ctg gcg cag atg cgc cgc atc tcg ctc ttc agc tgc ctg aag gac      96
Leu Leu Ala Gln Met Arg Arg Ile Ser Leu Phe Ser Cys Leu Lys Asp
             20                  25                  30 cgc cac gac ttc ggc ttc ccg cag gag gag ttc ggc aac cag ttc cag     144
```

-continued

```
                Arg His Asp Phe Gly Phe Pro Gln Glu Glu Phe Gly Asn Gln Phe Gln
                    35                  40                  45 aag gcc gag acg atc ccc gtg ctc cac gag atg atc cag cag atc ttc          192
Lys Ala Glu Thr Ile Pro Val Leu His Glu Met Ile Gln Gln Ile Phe
 50                  55                  60 aac ctg ttc agc acc aag gac agc tcg gcc gcc tgg gac gag acc ctg          240
Asn Leu Phe Ser Thr Lys Asp Ser Ser Ala Ala Trp Asp Glu Thr Leu
 65                  70                  75                  80 ctc gac aag ttc tac acc gag ctg tac cag cag ctc aac gac ctg gag          288
Leu Asp Lys Phe Tyr Thr Glu Leu Tyr Gln Gln Leu Asn Asp Leu Glu
                 85                  90                  95 gcg tgc gtg atc cag ggg gtt ggg gtt acg gag acg ccg ctg atg aag          336
Ala Cys Val Ile Gln Gly Val Gly Val Thr Glu Thr Pro Leu Met Lys
            100                 105                 110 gag gac agc atc ctc gcc gtg cgc aag tac ttc cag cgc atc acg ctc          384
Glu Asp Ser Ile Leu Ala Val Arg Lys Tyr Phe Gln Arg Ile Thr Leu
        115                 120                 125 tac ctc aag gag aag aag tac agc ccg tgc gcc tgg gag gtc gtt cgc          432
Tyr Leu Lys Glu Lys Lys Tyr Ser Pro Cys Ala Trp Glu Val Val Arg
    130                 135                 140 gcc gag atc atg cgc tcc ttc agc ctg agc acc aac ctc cag gag agc          480
Ala Glu Ile Met Arg Ser Phe Ser Leu Ser Thr Asn Leu Gln Glu Ser
145                 150                 155                 160 ctc cgc tcc aag gag taa                                                  498
Leu Arg Ser Lys Glu *
                165

<210> SEQ ID NO 3
<211> LENGTH: 96
<212> TYPE: DNA
<213> ORGANISM: Oryza sativa

<400> SEQUENCE: 3
accatgcagg tcctgaacac gatggtcaac aagcacttcc tctccctgtc cgtcctcatc        60
gtcctcctcg ggctgagcag caacctcacc gccggc                                  96

<210> SEQ ID NO 4
<211> LENGTH: 188
<212> TYPE: PRT
<213> ORGANISM: Homo sapiens

<400> SEQUENCE: 4

Met Ala Leu Thr Phe Ala Leu Leu Val Ala Leu Leu Val Leu Ser Cys
 1                   5                  10                  15

Lys Ser Ser Cys Ser Val Gly Cys Asp Leu Pro Gln Thr His Ser Leu
                 20                  25                  30

Gly Ser Arg Arg Thr Leu Met Leu Leu Ala Gln Met Arg Arg Ile Ser
             35                  40                  45

Leu Phe Ser Cys Leu Lys Asp Arg His Asp Phe Gly Phe Pro Gln Glu
         50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125
```

```
Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
        180                 185

<210> SEQ ID NO 5
<211> LENGTH: 165
<212> TYPE: PRT
<213> ORGANISM: Homo sapiens

<400> SEQUENCE: 5

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 6
<211> LENGTH: 31
<212> TYPE: PRT
<213> ORGANISM: Oryza sativa

<400> SEQUENCE: 6

Met Gln Val Leu Asn Thr Met Val Asn Lys His Phe Leu Ser Leu Ser
1               5                   10                  15

Val Leu Ile Val Leu Leu Gly Leu Ser Ser Asn Leu Thr Ala Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Modified rice alpha-amylase signal peptide

<400> SEQUENCE: 7

Met Gln Val Leu Asn Thr Met Val Asn Lys His Phe Leu Ser Leu Ser
1               5                   10                  15
```

Val Leu Ile Val Leu Thr Val Leu Ser Ser Asn Leu Thr Ala Gly
            20                  25                  30

<210> SEQ ID NO 8
<211> LENGTH: 21
<212> TYPE: PRT
<213> ORGANISM: Arabidopsis thaliana

<400> SEQUENCE: 8

Met Lys Thr Asn Leu Phe Leu Phe Leu Ile Phe Ser Leu Leu Leu Ser
1               5                   10                  15

Leu Ser Ser Ala Glu
            20

<210> SEQ ID NO 9
<211> LENGTH: 554
<212> TYPE: DNA
<213> ORGANISM: Zea mays

<400> SEQUENCE: 9
gatcaagtgc aaaggtccgc cttgtttctc ctctgtctct tgatctgact aatcttggtt     60
tatgattcgt tgagtaattt tggggaaagc ttcgtccaca gttttttttt cgatgaacag    120
tgccgcagtg cgctgatct tgtatgctat cctgcaatcg tggtgaactt atgtctttta    180
tatccttcac taccatgaaa agactagtaa tctttctcga tgtaacatcg tccagcactg    240
ctattaccgt gtggtccatc cgacagtctg gctgaacaca tcatacgata ttgagcaaag    300
atctatcttc cctgttcttt aatgaaagac gtcattttca tcagtatgat ctaagaatgt    360
tgcaacttgc aaggaggcgt ttctttcttt gaatttaact aactcgttga gtggccctgt    420
ttctcggacg taaggccttt gctgctccac acatgtccat tcgaatttta ccgtgtttag    480
caagggcgaa aagtttgcat cttgatgatt tagcttgact atgcgattgc tttcctggac    540
ccgtgcagct gcgg                                                      554

<210> SEQ ID NO 10
<211> LENGTH: 498
<212> TYPE: DNA
<213> ORGANISM: Homo sapiens

<400> SEQUENCE: 10
tgtgatctgc ctcaaaccca cagcctgggt agcaggagga ccttgatgct cctggcacag     60
atgaggagaa tctctctttt ctcctgcttg aaggacagac atgactttgg atttccccag    120
gaggagtttg caaccagtt ccaaaaggct gaaaccatcc ctgtcctcca tgagatgatc    180
cagcagatct tcaatctctt cagcacaaag gactcatctg ctgcttggga tgagaccctc    240
ctagacaaat tctacactga actctaccag cagctgaatg acctggaagc ctgtgtgata    300
caggggtgg gggtgacaga gactcccctg atgaaggagg actccattct ggctgtgagg    360
aaatacttcc aaagaatcac tctctatctg aaagagaaga atacagccc ttgtgcctgg    420
gaggttgtca gagcagaaat catgagatct ttttctttgt caacaaactt gcaagaaagt    480
ttaagaagta aggaatga                                                  498

<210> SEQ ID NO 11
<211> LENGTH: 569
<212> TYPE: DNA
<213> ORGANISM: Homo sapiens

<400> SEQUENCE: 11

```
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaagcc     360
tgtgtgatac aggggtggg ggtgacagag actccctga tgaaggagga ctccattctg       420
gctgtgagga aatacttcca aagaatcact ctctatctga aagagaagaa atacagccct     480
tgtgcctggg aggttgtcag agcagaaatc atgagatctt tttctttgtc aacaaacttg     540
caagaaagtt taagaagtaa ggaatgaaa                                       569

<210> SEQ ID NO 12
<211> LENGTH: 62
<212> TYPE: DNA
<213> ORGANISM: Arabidopsis thaliana

<400> SEQUENCE: 12
atgaagacta atctttttct ctttctcatc ttttcacttc tcctatcatt atcctcggcc      60
ga                                                                    62
```

EXPRESSION OF BIOLOGICALLY ACTIVE POLYPEPTIDE IN DUCKWEED

CROSS-REFERENCE TO RELATED APPLICATIONS

This application claims the benefit of U.S. Provisional Application Ser. No. 60/221,705, filed Jul. 31, 2000, and U.S. Provisional Application Ser. No. 60/293,330, filed May 23, 2001; each of which is hereby incorporated in its entirety by reference herein.

FIELD OF THE INVENTION

The present invention relates to methods and compositions for the expression and the secretion of biologically active polypeptides from genetically engineered duckweed.

BACKGROUND OF THE INVENTION

The duckweeds are the sole members of the monocotyledonous family Lemnaceae. The four genera and 34 species are all small, free-floating, fresh-water plants whose geographical range spans the entire globe (Landolt (1986) *Biosystematic Investigation on the Family of Duckweeds: The Family of Lemnaceae—A Monograph Study* Geobatanischen Institut ETH, Stiftung Rubel, Zurich). Although the most morphologically reduced plants known, most duckweed species have all the tissues and organs of much larger plants, including roots, stems, flowers, seeds and fronds. Duckweed species have been studied extensively and a substantial literature exists detailing their ecology, systematics, life-cycle, metabolism, disease and pest susceptibility, their reproductive biology, genetic structure, and cell biology. (Hillman (1961) *Bot. Review* 27:221; Landolt (1986) *Biosystematic Investigation on the Family of Duckweeds: The Family of Lemnaceae—A Monograph Study* Geobatanischen Institut ETH, Stiftung Rubel, Zurich).

The growth habit of the duckweeds is ideal for microbial culturing methods. The plant rapidly proliferates through vegetative budding of new fronds, in a macroscopic manner analogous to asexual propagation in yeast. This proliferation occurs by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20–24 hours (Landolt (1957) *Ber. Schweiz. Bot. Ges.* 67:271; Chang et al. (1977) *Bull. Inst. Chem. Acad. Sin.* 24:19; Datko and Mudd (1970) *Plant Physiol.* 65:16; Venkataraman et al. (1970) *Z. Pflanzenphysiol.* 62:316).

Intensive culture of duckweed results in the highest rates of biomass accumulation per unit time (Landolt and Kandeler (1987) *The Family of Lemnaceae—A Monographic Study Vol. 2: Phytochemistry, Physiology, Application, Bibliography*, Veroffentlichungen des Geobotanischen Institutes ETH, Stiftung Rubel, Zurich), with dry weight accumulation ranging from 6–15% of fresh weight (Tillberg et al. (1979) *Physiol. Plant.* 46:5; Landolt (1957) *Ber. Schweiz. Bot. Ges.* 67:271; Stomp, unpublished data). Protein content of a number of duckweed species grown under varying conditions has been reported to range from 15–45% dry weight (Chang et al (1977) *Bull. Inst. Chem. Acad. Sin.* 24:19; Chang and Chui (1978) *Z. Pflanzenphysiol.* 89:91; Porath et al. (1979) *Aquatic Botany* 7:272; Appenroth et al. (1982) *Biochem. Physiol. Pflanz.* 177:251). Using these values, the level of protein production per liter of medium in duckweed is on the same order of magnitude as yeast gene expression systems.

Sexual reproduction in duckweed is controlled by medium components and culturing conditions, including photoperiod and culture density. Flower induction is a routine laboratory procedure with some species. Plants normally self-pollinate, and selfing can be accomplished in the laboratory by gently shaking cultures. By this method, inbred lines of *Lemna gibba* have been developed. Spontaneous mutations have been identified (Slovin and Cohen (1988) *Plant Physiol.* 86, 522), and chemical and gamma ray mutagenesis (using EMS or NMU) have been used to produce mutants with defined characteristics. Outcrossing of *L. gibba* is tedious but can be done by controlled, hand pollination. The genome size of the duckweeds varies from 0.25–1.63 pg DNA/2C with chromosome counts ranging from 20 to 80 and averaging about 40 across the Lemnaceae (Landolt (1986) *Biosystematic Investigation on the Family of Duckweeds: The family of Lemnaceae—A Monograph Study* Geobatanischen Institut ETH, Stiftung Rubel, Zurich). Ploidy levels are estimated to range from 2–12 C. Id. Genetic diversity within the Lemnaceae has been investigated using secondary products, isozymes, and DNA sequences (McClure and Alston (1966) *Nature* 4916:311; McClure and Alston (1966) *Amer. J. Bot.* 53:849; Vasseur et al. (1991) *Pl. Syst. Evol.* 177:139 (1991); Crawford and Landolt (1993) *Syst. Bot.* 10:389).

Duckweed plant or duckweed nodule cultures can be efficiently transformed with an expression cassette containing a nucleotide sequence of interest by any one of a number of methods including *Agrobacterium*-mediated gene transfer, ballistic bombardment, or electroporation. Stable duckweed transformants can be isolated by transforming the duckweed cells with both the nucleotide sequence of interest and a gene which confers resistance to a selection agent, followed by culturing the transformed cells in a medium containing the selection agent. See U.S. Pat. No. 6,040,498 to Stomp et al.

A duckweed gene expression system provides the pivotal technology that would be useful for a number of research and commercial applications. For plant molecular biology research as a whole, a differentiated plant system that can be manipulated with the laboratory convenience of yeast provides a very fast system in which to analyze the developmental and physiological roles of isolated genes. For commercial production of valuable polypeptides, a duckweed-based system has a number of advantages over existing microbial or cell culture systems. Plants demonstrate post-translational processing that is similar to mammalian cells, overcoming one major problem associated with the microbial cell production of biologically active mammalian polypeptides, and it has been shown by others (Hiatt (1990) *Nature* 334:469) that plant systems have the ability to assemble multi-subunit proteins, an ability often lacking in microbial systems. Scale-up of duckweed biomass to levels necessary for commercial production of recombinant proteins is faster and more cost efficient than similar scale-up of mammalian cells, and unlike other suggested plant production systems, e.g., soybeans and tobacco, duckweed can be grown in fully contained and controlled biomass production vessels, making the system's integration into existing protein production industrial infrastructure far easier.

These characteristics make duckweed an ideal choice to develop as an efficient, plant-based system for the production of recombinant proteins. Accordingly, the present invention provides methods and compositions that increase the efficiency of the duckweed gene expression system as a tool for producing biologically active polypeptides.

SUMMARY OF THE INVENTION

The present invention is drawn to methods and compositions for the expression and recovery of biologically active recombinant polypeptides, using duckweed as the expression system. One aspect of the present invention provides a method for enhanced expression levels of biologically active polypeptides in duckweed, resulting in an increased polypeptide yield and enabling the production of useful quantities of valuable biologically active polypeptides in this system. Another aspect of the invention discloses methods for the directed secretion of biologically active polypeptides from genetically engineered duckweed plant or duckweed nodule cultures. Secretion of the expressed polypeptide facilitates its recovery and prevents the loss of activity that might result from the mechanical grinding or enzymatic lysing of the duckweed tissue.

In one embodiment, the invention encompasses a method of producing a biologically active recombinant polypeptide in a duckweed plant culture or a duckweed nodule culture, comprising the steps of: (a) culturing within a duckweed culture medium a duckweed plant culture or a duckweed nodule culture, wherein said duckweed plant culture or said duckweed nodule culture is stably transformed to express said biologically active recombinant polypeptide, and wherein said biologically active recombinant polypeptide is expressed from a nucleotide sequence comprising a coding sequence for the polypeptide and an operably linked coding sequence for a signal peptide that directs secretion of the polypeptide into the culture medium; and (b) collecting said biologically active polypeptide from the duckweed culture medium. In some embodiments of this method, the nucleotide sequence has at least one attribute selected from the group consisting of: (a) duckweed-preferred codons in the coding sequence for said polypeptide; (b) duckweed-preferred codons in the coding sequence for said signal peptide; (c) a translation initiation codon that is flanked by a plant-preferred translation initiation context nucleotide sequence; and (d) an operably linked nucleotide sequence comprising a plant intron that is inserted upstream of the coding sequence. In some embodiments of this method, the biologically active recombinant polypeptide is secreted into the duckweed culture medium.

In another embodiment, the invention encompasses a method of secreting a biologically active recombinant polypeptide in a duckweed plant culture or a duckweed nodule culture, comprising the steps of: (a) culturing within a duckweed culture medium a duckweed plant culture or a duckweed nodule culture, wherein said duckweed plant culture or said duckweed nodule culture is stably transformed to express said biologically active recombinant polypeptide, and wherein said biologically active recombinant polypeptide is expressed from a nucleotide sequence comprising a coding sequence for the polypeptide and an operably linked coding sequence for a signal peptide that directs secretion of the polypeptide into the culture medium; and (b) collecting said biologically active polypeptide from the duckweed culture medium. In some embodiments of this method, the nucleotide sequence has at least one attribute selected from the group consisting of: (a) duckweed-preferred codons in the coding sequence for said polypeptide; (b) duckweed-preferred codons in the coding sequence for said signal peptide; (c) a translation initiation codon that is flanked by a plant-preferred translation initiation context nucleotide sequence; and (d) an operably linked nucleotide sequence comprising a plant intron that is inserted upstream of the coding sequence. In some embodiments of this method, the biologically active recombinant polypeptide is secreted into the duckweed culture medium.

In some embodiments of the above methods, the signal peptide is selected from the group consisting of: (a) the human α-2b-interferon signal sequence; (b) the *Arabidopsis thaliana* chitinase signal sequence; (c) the rice α-amylase signal sequence; (d) the modified rice α-amylase sequence; (e) a duckweed signal sequence; and (f) a signal sequence native to the biologically active recombinant polypeptide. In one embodiment of the method, the signal peptide is the rice α-amylase signal peptide whose sequence is set forth in SEQ ID NO:3.

In some embodiments of the above methods, the duckweed-preferred codons are *Lemna*-preferred codons. In further embodiments, the duckweed-preferred codons are *Lemna gibba*-preferred codons or *Lemna minor*-preferred codons. In further embodiments, at least one coding sequence selected from the coding sequence for the biologically active recombinant polypeptide and the coding sequence for the signal peptide comprises between 70–100% *Lemna gibba*-preferred codons or *Lemna minor*-preferred codons.

In other embodiments, the invention encompasses a method of producing a biologically active recombinant polypeptide, comprising the steps of: (a) culturing a duckweed plant culture or a duckweed nodule culture, wherein said duckweed plant culture or said duckweed nodule culture is stably transformed to express said biologically active recombinant polypeptide, and wherein said biologically active recombinant polypeptide is encoded by a nucleotide sequence that has been modified for enhanced expression in duckweed, and (b) collecting said biologically active polypeptide from said duckweed plant culture or said duckweed nodule culture. In some embodiments of this method, the nucleotide sequence that has been modified for enhanced expression in duckweed has at least one attribute selected from the group consisting of: (a) duckweed-preferred codons in the coding sequence for said biologically active recombinant polypeptide; (b) a translation initiation codon that is flanked by a plant-preferred translation initiation context nucleotide sequence; and (c) an operably linked nucleotide sequence comprising a plant intron that is inserted upstream of the coding sequence.

In some embodiments of this method, the duckweed-preferred codons are *Lemna*-preferred codons. In further embodiments, the duckweed-preferred codons are *Lemna gibba*-preferred codons or *Lemna minor*-preferred codons. In further embodiments, the coding sequence comprises between 70–100% *Lemna gibba*-preferred codons or *Lemna minor*-preferred codons.

In some embodiments of the above methods, the plant-preferred translation initiation context nucleotide sequence consists of the nucleotide sequence "ACC" or "ACA", wherein said context is positioned immediately adjacent to the 5' end of the translation initiation codon.

In some embodiments of the above methods, the operably linked nucleotide sequence comprising said plant intron is the sequence set forth in SEQ ID NO:1.

In some embodiments of any of the above methods, the duckweed frond culture or duckweed nodule culture expresses and assembles all of the subunits of a biologically active multimeric protein. In further embodiments, the multimeric protein is selected from the group consisting of collagen, hemoglobin, P450 oxidase, and a monoclonal antibody.

In some embodiments of any of the above methods, the biologically active recombinant polypeptide is a mammalian polypeptide. In further embodiments, the mammalian polypeptide is a therapeutic polypeptide. In some embodiments, the mammalian polypeptide is selected from the group consisting of: insulin, growth hormone, α-interferon, β-interferon, β-glucocerebrosidase, β-glucoronidase, retinoblastoma protein, p53 protein, angiostatin, leptin, monoclonal antibodies, cytokines, receptors, human vaccines, animal vaccines, plant polypeptides, and serum albumin.

In some embodiments of any of the above methods, the biologically active recombinant polypeptide is α-2b-interferon. In further embodiments, the α-2b-interferon is human α-2b-interferon. In further embodiments, the human α-2b-interferon has the amino acid sequence set forth in SEQ ID NO:4 or SEQ ID NO:5.

In some embodiments of any of the above methods, the biologically active recombinant polypeptide is a biologically active variant of α-2b-interferon, wherein said biologically active variant has at least 80% sequence identity with SEQ ID NO:4 or SEQ ID NO:5.

In some embodiments of any of the above methods, the biologically active recombinant polypeptide is an enzyme.

In other embodiments, the invention encompasses the stably transformed duckweed plant culture or duckweed nodule culture of any of the above methods. In further embodiments, the stably transformed duckweed plant culture or duckweed nodule culture is selected from the group consisting of the genus Spirodela, genus Wolffia, genus Wolfiella, and genus *Lemna*. In further embodiments, the stably transformed duckweed plant culture or duckweed nodule culture is selected from the group consisting of *Lemna minor, Lemna miniscula, Lemna aequinoctialis*, and *Lemna gibba*.

In other embodiments, the invention encompasses a nucleic acid molecule comprising a nucleotide sequence encoding an amino acid sequence selected from the group consisting of: (a) the amino acid sequence set forth in SEQ ID NO:4; (b) the amino acid sequence set forth in SEQ ID NO:5; (c) the amino acid sequence of a biologically active variant of the amino acid sequence shown in SEQ ID NO:4, wherein said biologically active variant has at least about 80% sequence identity with the amino acid sequence set forth in SEQ ID NO:4; and (d) the amino acid sequence of a biologically active variant of the amino acid sequence shown in SEQ ID NO:5, wherein said biologically active variant has at least about 80% sequence identity with the amino acid sequence set forth in SEQ ID NO:5; wherein the nucleotide sequence comprises duckweed-preferred codons. In further embodiments, the nucleotide sequence is the nucleotide sequence set forth in SEQ ID NO:2.

In other embodiments, the invention encompasses a nucleic acid molecule comprising a nucleotide sequence encoding a signal peptide selected from the group consisting of: (a) the rice α-amylase signal peptide amino acid sequence set forth in SEQ ID NO:6; and (b) the modified rice-amylase signal peptide amino acid sequence set forth in SEQ ID NO:7; wherein the nucleotide sequence comprises duckweed-preferred codons. In further embodiments, the nucleotide sequence is the nucleotide sequence set forth in SEQ ID NO:3.

In other embodiments, the invention encompasses a nucleic acid molecule for the expression and secretion of human α-2b-interferon in duckweed comprising the signal peptide-encoding nucleotide sequence given in SEQ ID NO:3, and the mature human α-2b-interferon-encoding nucleotide sequence given in SEQ ID NO:5, wherein the signal peptide-encoding nucleotide sequence and said mature human α-2b-interferon-encoding nucleotide sequence are operably linked. In further embodiments, the nucleic acid molecule additionally comprises the intron-comprising nucleotide sequence given in SEQ ID NO:1, wherein said intron-comprising nucleotide sequence is operably linked to said signal peptide-encoding nucleotide sequence and said mature human α-2b-interferon-encoding nucleotide sequence.

These and other aspects of the present invention are disclosed in more detail in the description of the invention given below.

BRIEF DESCRIPTION OF THE DRAWINGS

FIG. 1

FIG. 2

DETAILED DESCRIPTION OF THE INVENTION

In the present invention, methods are disclosed for improving the expression and the recovery of biologically active polypeptides from genetically engineered duckweed plants and duckweed nodule cultures. These methods comprise the steps of (1) culturing a stably transformed duckweed plant or a duckweed nodule culture that expresses at least one biologically active polypeptide, wherein the polypeptide is encoded by a nucleotide sequence that has been modified for enhanced expression in duckweed, and recovering the biologically active polypeptide from the duckweed culture. Modifications to the nucleotide sequence that are encompassed by this invention include, but are not limited to, the use of duckweed-preferred codons for the coding sequence, the use of a plant-preferred translation initiation context nucleotide sequence for the translation initiation codon, and the insertion of a nucleotide sequence comprising a plant intron sequence upstream of the sequence encoding the polypeptide.

(2) Culturing a stably transformed duckweed plant or duckweed nodule culture that expresses at least one biologically active polypeptide comprising a signal sequence that directs secretion of the polypeptide into the culture medium, followed by recovering the biologically active polypeptide from the culture medium. In one embodiment of this method, the nucleotide sequence encoding the biologically active polypeptide is modified for enhanced expression in duckweed. Alternatively, in another embodiment the nucleotide sequence encoding the signal peptide is modified for enhanced expression in duckweed. In one embodiment, the nucleotide sequence encoding both the biologically active polypeptide and the signal peptide are modified for enhanced expression in duckweed.

As another aspect, the present invention encompasses transformed duckweed plants or duckweed nodule cultures producing biologically active polypeptides according to the methods above.

As another aspect, the present invention discloses methods and nucleic acid sequences for producing biologically active human α-2b-interferon in duckweed.

Definitions

"Polypeptide" refers to any monomeric or multimeric protein or peptide.

"Biologically active polypeptide" refers to a polypeptide that has the capability of performing one or more biological functions or a set of activities normally attributed to the polypeptide in a biological context. Those skilled in the art will appreciate that the term "biologically active" includes polypeptides in which the biological activity is altered as compared with the native protein (e.g., suppressed or enhanced), as long as the protein has sufficient activity to be of interest for use in industrial or chemical processes or as a therapeutic, vaccine, or diagnostics reagent. Biological activity can be determined by any method available in the art. For example, the biological activity of members of the interferon family of proteins can be determined by any of a number of methods including their interaction with interferon-specific antibodies, their ability to increase resistance to viral infection, or their ability to modulate the transcription of interferon-regulated gene targets.

"Nucleotide sequence of interest" as used herein refers to any nucleotide sequence encoding a polypeptide intended for expression in duckweed. For example, nucleotide sequences encoding therapeutic (e.g., for veterinary or medical uses) or immunogenic (e.g., for vaccination) polypeptides can be expressed using transformed duckweed according to the present invention.

The terms "expression" or "production" refer to the biosynthesis of a gene product, including the transcription, translation, and assembly of said gene product.

The term "duckweed" refers to members of the family Lemnaceae. This family currently is divided into four genera and 34 species of duckweed as follows: genus Lemna (L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana); genus Spirodela (S. intermedia, S. polyrrhiza, S. punctata); genus Wolffia (Wa. angusta, Wa. arrhiza, Wa. australina, Wa. borealis, Wa. brasiliensis, Wa. columbiana, Wa. elongata, Wa. globosa, Wa. microscopical Wa. neglecta) and genus Wolfiella (Wl. caudata, Wl. denticulata, Wl. gladiata, Wl. hyalina, Wl. lingulata, Wl. repunda, Wl. rotunda, and Wl. neotropica). Any other genera or species of Lemnaceae, if they exist, are also aspects of the present invention. Lemna species can be classified using the taxonomic scheme described by Landolt (1986) Biosystematic Investigation on the Family of Duckweeds: The family of Lemnaceae—A Monograph Study Geobatanischen Institut ETH, Stiftung Rubel, Zurich.

The term "duckweed nodule culture" as used herein refers to a culture comprising duckweed cells wherein at least about 50%, 55%, 60%, 65%, 70%, 75%, 80%, 85%, 90%, 95%, or 100% of the cells are differentiated cells. A "differentiated cell," as used herein, is a cell with at least one phenotypic characteristic (e.g., a distinctive cell morphology or the expression of a marker nucleic acid or protein) that distinguishes it from undifferentiated cells or from cells found in other tissue types. The differentiated cells of the duckweed nodule culture described herein form a tiled smooth surface of interconnected cells fused at their adjacent cell walls, with nodules that have begun to organize into frond primordium scattered throughout the tissue. The surface of the tissue of the nodule culture has epidermal cells connect to each other via plasmadesmata.

"Duckweed-preferred codons" as used herein refers to codons that have a frequency of codon usage in duckweed of greater than 17%.

"Lemna-preferred codons" as used herein refers to codons that have a frequency of codon usage in the genus Lemna of greater than 17%.

"Lemna gibba-preferred codons" as used herein refers to codons that have a frequency of codon usage in Lemna gibba of greater than 17% where the frequency of codon usage in Lemna gibba was obtained from the Codon Usage Database (GenBank Release 113,0; see Table 5.

"Translation initiation codon" refers to the codon that initiates the translation of the mRNA transcribed from the nucleotide sequence of interest.

"Translation initiation context nucleotide sequence" as used herein refers to the identity of the three nucleotides directly 5' of the translation initiation codon.

"Secretion" as used herein refers to translocation of a polypeptide across both the plasma membrane and the cell wall of a host plant cell.

"Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame.

A. Expression Cassettes

According to the present invention, stably transformed duckweed is obtained by transformation with a nucleotide sequence of interest contained within an expression cassette. The expression cassette comprises a transcriptional initiation region linked to the nucleic acid or gene of interest. Such an expression cassette is provided with a plurality of restriction sites for insertion of the gene or genes of interest (e.g., one gene of interest, two genes of interest, etc.) to be under the transcriptional regulation of the regulatory regions. The expression cassette may encode a single gene of interest. In particular embodiments of the invention, the nucleic acid to be transferred contains two or more expression cassettes, each of which encodes at least one gene of interest.

The transcriptional initiation region, (e.g., a promoter) may be native or homologous or foreign or heterologous to the host, or could be the natural sequence or a synthetic sequence. By foreign, it is intended that the transcriptional initiation region is not found in the wild-type host into which the transcriptional initiation region is introduced. As used herein a chimeric gene comprises a coding sequence operably linked to a transcription initiation region that is heterologous to the coding sequence.

Any suitable promoter known in the art can be employed according to the present invention (including bacterial, yeast, fungal, insect, mammalian, and plant promoters). For example, plant promoters, including duckweed promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthorne et al. (1990) Plant Mol. Biol. 15:49). Other promoters from viruses that infect plants, preferably duckweed, are also suitable including, but not limited to, promoters isolated from Dasheen mosaic virus, Chlorella virus (e.g., the Chlorella virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Finally, promoters can be chosen to give a desired level of regulation. For example, in some instances, it may be advantageous to use a promoter that confers constitutive expression (e.g, the mannopine synthase promoter from *Agrobacterium tumefaciens*). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646 to Gelvin et al). In the present invention, the expression cassette can contain activating nucleotide sequences inserted upstream of the promoter sequence to enhance the expression of the nucleotide sequence of interest. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955, 646, herein incorporated by reference).

The transcriptional cassette includes in the 5'-3' direction of transcription, a transcriptional and translational initiation region, a nucleotide sequence of interest, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence. Other suitable termination sequences will be apparent to those skilled in the art.

Alternatively, the gene(s) of interest can be provided on any other suitable expression cassette known in the art.

The expression cassettes may contain more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) *EMBO J.* 6:2513; DeBlock et al.(1989) *Plant Physiol.* 91:691; Fromm et al. (1990) *BioTechnology* 8:833; Gordon-Kamm et al. (1990) *Plant Cell* 2:603. For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) *CRC Critical Reviews in Plant Science* 4:1); cyanamide hydratase (Maier-Greiner et al (1991) *Proc. Natl. Acad. Sci. USA* 88:4250); aspartate kinase; dihydrodipicolinate synthase (Perl et al. (1993) *BioTechnology* 11:715); bar gene (Toki et al (1992) *Plant Physiol.* 100:1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761,373 to Anderson et al.; Haughn et al. (1988) *Mol. Gen. Genet.* 221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to: gentamycin (e.g., aacC1, Wohlleben et al. (1989) *Mol. Gen. Genet.* 217:202–208); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Bio.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Bio.* 15:127); bromoxynil (Stalker et al. (1988) *Science* 242:419); 2,4-D (Streber et al. (1989) *BioTechnology* 7:811); phosphinothricin (DeBlock et al. (1987) *EMBO J.* 6:2513); spectinomycin (Bretagne-Sagnard and Chupeau, *Transgenic Research* 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff(1992) *Mol. Microbiol.* 6:2419; Barkley et al. (1980) *The Operon* 177–220; Hu et al (1987) *Cell* 48:555; Brown et al. (1987) *Cell* 49:603; Figge et al. (1988) *Cell* 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al. (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes are not meant to be limiting. Any selectable marker gene can be used in the present invention.

B. Modification of Nucleotide Sequences for Enhanced Expression in Duckweed

The present invention provides for the modification of the expressed nucleotide sequence to enhance its expression in duckweed. One such modification is the synthesis of the nucleotide sequence of intrest using duckweed-preferred codons. Methods are available in the art for synthesizing nucleotide sequences with plant-preferred codons. See, e.g., U.S. Pat. Nos. 5,380,831 and 5,436,391; Perlak et al. (1991) *Proc. Natl. Acad. Sci. USA* 15:3324; lannacome et al. (1997) *Plant Mol. Biol.* 34:485; and Murray et al., (1989) *Nucleic Acids. Res.* 17:477, herein incorporated by reference. The preferred codons may be determined from the codons of highest frequency in the proteins expressed in duckweed. For example, the frequency of codon usage for *Lemna gibba* for GenBank Release 113.0 is found in Table 5. It is recognized that genes which have been optimized for expression in duckweed and other monocots can be used in the methods of the invention. See, e.g., EP 0 359 472, EP 0 385 962, WO 91/16432; Perlak et al. (1991) *Proc. Natl. Acad. Sci. USA* 88:3324; lannacome et al. (1997) *Plant Mol. Biol.* 34:485; and Murray et al. (1989) *Nuc. Acids Res.* 17:477, and the like, herein incorporated by reference. It is further recognized that all or any part of the gene sequence may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be duckweed-preferred codons. In one embodiment, between 90 and 96% of the codons are duckweed-preferred codons. The coding sequence of the nucleotide sequence of interest may comprise codons used with a frequency of at least 17% in *Lemna gibba*. In one embodiment, the modified nucleotide sequence is the human α-2B-interferon encoding nucleotide sequence shown in SEQ ID NO:2, which contains 93% duckweed preferred codons.

Other modifications can also be made to the nucleotide sequence of interest to enhance its expression in duckweed. These modifications include, but are not limited to, elimination of sequences encoding spurious polyadenylation signals, exon-intron splice site signals, transposon-like repeats, and other such well characterized sequences which may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

There are known differences between the optimal translation initiation context nucleotide sequences for translation initiation codons in animals and plants and the composition of these translation initiation context nucleotide sequence can influence the efficiency of translation initiation. See, for example, Lukaszewicz et al. (2000) *Plant Science* 154:89–98; and Joshi et al. (1997); *Plant Mol. Biol.* 35:993–1001. In the present invention, the translation initiation context nucleotide sequence for the translation initiation codon of the nucleotide sequence of interest may be modified to enhance expression in duckweed. In one embodiment, the nucleotide sequence is modified such that the three nucleotides directly upstream of the translation initiation codon of the nucleotide sequence of interest are "ACC." In a second embodiment, these nucleotides are "ACA."

Expression of a transgene in duckweed can also be enhanced by the use of 5' leader sequences. Such leader sequences can act to enhance translation. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA*, 23:56); potato etch virus leader (Tomashevskaya et al. (1993) *J. Gen. Virol.* 74:2717–2724); Fed-1 5' untranslated region (Dickey (1992) *EMBO J.* 11:2311–2317); RbcS 5' untranslated region (Silverthorne et al. (1990) *J. Plant. Mol. Biol.* 15:49–58); and maize chlorotic mottle virus leader (MCMV; Lommel et al. (1991) *Virology* 81:382). See also, Della-Cioppa et al. (1987) *Plant Physiology* 84:965. Leader sequence comprising plant intron sequence, including intron sequence from the maize dehydrogenase 1 gene, the castor bean catalase gene, or the Arabidopsis tryptophan pathway gene PAT1 has also been shown to increase translational efficient in plants (Callis et al. (1987) *Genes Dev.* 1:1183–1200; Mascarenhas et al. (1990) *Plant Mol. Biol.* 15:913–920). In one embodiment of the present invention, nucleotide sequence corresponding to nucleotides 1222–1775 of the maize alcohol dehydrogenase 1 gene (GenBank Accession Number X04049), set forth in SEQ ID NO:1, is inserted upstream of the nucleotide sequence of interest to enhance the efficiency of its translation.

It is recognized that any of the duckweed expression-enhancing nucleotide sequence modifications described above can be used in the present invention, including any single modification or any possible combination of modifications. The phrase "modified for enhanced expression in duckweed" as used herein refers to a nucleotide sequence that contains any one or any combination of these modifications.

C. Signal Peptides

Secreted proteins are usually translated from precursor polypeptides that include a "signal peptide" that interacts with a receptor protein on the membrane of the endoplasmic reticulum (ER) to direct the translocation of the growing polypeptide chain across the membrane and into the endoplasmic reticulum for secretion from the cell. This signal peptide is often cleaved from the precursor polypeptide to produce a "mature" polypeptide lacking the signal peptide. In an embodiment of the present invention, a biologically active polypeptide is expressed in duckweed from a nucleotide sequence that is operably linked with a nucleotide sequence encoding a signal peptide that directs secretion of the polypeptide into the culture medium. Plant signal peptides that target protein translocation to the endoplasmic reticulum (for secretion outside of the cell) are known in the art. See, for example, U.S. Pat. No. 6,020,169 to Lee et al. In the present invention, any plant signal peptide can be used to in target polypeptide expression to the ER. In some embodiments, the signal peptide is the *Arabidopsis thaliana* basic endochitinase signal peptide (SEQ ID NO:8; amino acids 14–34 of NCBI Protein Accession No. BAA82823), the extensin signal peptide (Stiefel et al. (1990) *Plant Cell* 2:785–793), the rice α-amylase signal peptide (SEQ ID NO:6; amino acids 1–31 of NCBI Protein Accession No. AAA33885), or a modified rice α-amylase signal sequence (SEQ ID NO:7). In another embodiment, the signal peptide corresponds to the signal peptide of a secreted duckweed protein.

Alternatively, a mammalian signal peptide can be used to target recombinant polypeptides expressed in genetically engineered duckweed for secretion. It has been demonstrated that plant cells recognize mammalian signal peptides that target the endoplasmic reticulum, and that these signal peptides can direct the secretion of polypeptides not only through the plasma membrane but also through the plant cell wall. See U.S. Pat. Nos. 5,202,422 and 5,639,947 to Hiatt et al. In one embodiment of the present invention, the mammalian signal peptide that targets polypeptide secretion is the human α-2b-interferon signal peptide (amino acids 1–23 of NCBI Protein Accession No. AAB59402 and SEQ ID NO:4).

In one embodiment, the nucleotide sequence encoding the signal peptide is modified for enhanced expression in duckweed, utilizing any modification or combination of modifications disclosed in section B above for the nucleotide sequence of interest. In another embodiment, the signal peptide the rice α-amylase encoded by the modified nucleotide sequence set forth in SEQ ID NO:3, which contains approximately 93% duckweed preferred codons.

The secreted biologically active polypeptide can be harvested from the culture medium by any conventional means known in the art and purified by chromatography, electrophoresis, dialysis, solvent-solvent extraction, and the like.

D. Transformed Duckweed Plants and Duckweed Nodule Cultures

The stably transformed duckweed utilized in this invention can be obtained by any method known in the art. In one embodiment, the stably transformed duckweed is obtained by one of the gene transfer methods disclosed in U.S. Pat. No. 6,040,498 to Stomp et al., herein incorporated by reference. These methods include gene transfer by ballistic bombardment with microprojectiles coated with a nucleic acid comprising the nucleotide sequence of interest, gene transfer by electroporation, and gene transfer mediated by *Agrobacterium* comprising a vector comprising the nucleotide sequence of interest. In one embodiment, the stably transformed duckweed is obtained via any one of the *Agrobacterium*-mediated methods disclosed in U.S. Pat. No. 6,040,498 to Stomp et al. The *Agrobacterium* used is *Agrobacterium tumefaciens* or *Agrobacterium rhizogenes*.

It is preferred that the stably transformed duckweed plants utilized in these methods exhibit normal morphology and are fertile by sexual reproduction. Preferably, transformed plants of the present invention contain a single copy of the transferred nucleic acid, and the transferred nucleic acid has no notable rearrangements therein. Also preferred are duckweed plants in which the transferred nucleic acid is present in low copy numbers (i.e., no more than five copies, alternately, no more than three copies, as a further alternative, fewer than three copies of the nucleic acid per transformed cell).

The stably transformed duckweed expresses a biologically active protein hormone, growth factor, or cytokine, insulin, or growth hormone (in particular, human growth hormone). Alternatively, the duckweed expresses biologically active β-glucuronidase. The duckweed may express biologically active α-2b-interferon, for example human α-2b-interferon precursor (NCBI Protein Accession No. AAB59402; set forth in SEQ ID NO:4) or mature human α-2b-interferon (amino acids 24–188 of NCBI Protein Accession No. AAB9402; set forth in SEQ ID NO:5) or biologically active variants thereof.

By "biologically active variant" of human α-2b-interferon is intended a polypeptide derived from the native polypeptide by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Biologically active variant α-2b-interferon polypeptides encompassed by the present invention are biologically active, that is they continue to possess the desired biological activity of the native α-2b-interferon including the ability to increase resistance to viral infection, or the ability to modulate the transcription of α-2b-interferon-regulated gene targets. Such biologically active variants may result from, for example, genetic polymorphism or from human manipulation. Biologically active variants of a native α-2b-interferon protein of the invention will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence shown in SEQ ID NO:4 or SEQ ID NO:5. Thus, a biologically active variant of an α-2b-interferon of the invention may differ from that protein by as few as 1–15 amino acid residues, as few as 1–10, such as 6–10, as few as 5, as few as 4, 3, 2, or even 1 amino acid residue. Examples of biologically active variants of human α-interferon are known in the art. See, for example, European patent EP211148B1, and U.S. Pat. Nos. 4,748,233, 4,801,685, 4,816,566, 4,973,479, 4,975,276, 5,089,400, 5,098,703, 5,231,176, and 5,869,293; herein incorporated by reference.

The comparison of sequences and determination of percent identity and percent similarity between two sequences can be accomplished using a mathematical algorithm. In a preferred embodiment, the percent identity between two amino acid sequences is determined using the Needleman and Wunsch (1970) *J. Mol. Biol.* 48:444–453 algorithm, which is incorporated into the GAP program in the GCG software package (available at www.accelrys.com), using either a BLOSSUM62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a BLOSUM62 scoring matrix (see Henikof- fet al. (1989) *Proc. Natl. Acad. Sci. USA* 89:10915) and a gap weight of 40, 50, 60, 70, or 80 and a length weight of 1, 2, 3, 4, 5, or 6. A particularly preferred set of parameters (and the one that should be used if the practitioner is uncertain about what parameters should be applied to deter- mine if a molecule is within a sequence identity limitation of the invention) is using a BLOSUM62 scoring matrix with a gap weight of 60 and a length weight of 3).

The percent identity between two amino acid or nucle- otide sequences can also be determined using the algorithm of E. Meyers and W. Miller (1989) *CABIOS* 4:11–17 which has been incorporated into the ALIGN program (version 2.0), using a PAM120 weight residue table, a gap length penalty of 12 and a gap penalty of 4.

In one embodiment, the stably transformed duckweed plants or duckweed nodule cultures express biologically active polypeptides that cannot effectively be commercially produced by existing gene expression systems, because of cost or logistical constraints, or both. For example, some proteins cannot be expressed in mammalian systems because the protein interferes with cell viability, cell proliferation, cellular differentiation, or protein assembly in mammalian cells. Such proteins include, but are not limited to, retino- blastoma protein, p53, angiostatin, and leptin. The present invention can be advantageously employed to produce mam- malian regulatory proteins; it is unlikely given the large evolutionary distance between higher plants and mammals that these proteins will interfere with regulatory processes in duckweed. Transgenic duckweed can also be used to pro- duce large quantities of proteins such as serum albumin (in particular, human serum albumin), hemoglobin, and collagen, which challenge the production capabilities of existing expression systems.

Finally, higher plant systems can be engineered to pro- duce biologically active multimeric proteins (e.g., mono- clonal antibodies, hemoglobin, P450 oxidase, and collagen, and the like) far more easily than can mammalian systems. One exemplary approach for producing biologically active multimeric proteins in duckweed uses an expression vector containing the genes encoding all of the polypeptide sub- units. See, e.g., During et al. (1990) *Plant Mol. Biol.* 15:281 and van Engelen et al. (1994) *Plant Mol. Biol.* 26:1701. This vector is then introduced into duckweed cells using any known transformation method, such as a ballistic bombard- ment or *Agrobacterium*-mediated transformation. This method results in clonal cell lines that express all of the polypeptides necessary to assemble the multimeric protein. A variation on this approach is to make single gene constructs, mix DNA from these constructs together, then deliver this mixture of DNAs into plant cells using ballistic bombardment or *Agrobacterium*-mediated transformation. As a further variation, some or all of the vectors may encode more than one subunit of the multimeric protein (i.e., so that there are fewer duckweed clones to be crossed than the number of subunits in the multimeric protein). In an alter- native embodiment, each duckweed clone expresses at least one of the subunits of the multimeric protein, and duckweed clones secreting each subunit are cultured together and the multimeric protein is assembled in the media from the various secreted subunits. In some instances, it may be desirable to produce less than all of the subunits of a multimeric protein, or even a single protein subunit, in a transformed duckweed plant or duckweed nodule culture, e.g., for industrial or chemical processes or for diagnostic, therapeutic, or vaccination purposes.

EXPERIMENTAL

The following examples are offered for purposes of illustration, not by way of limitation Expression Vectors The expression vector pBMSP-1 used in some of the examples is described in U.S. Pat. No. 5,955,646, herein incorporated by reference. The pBMSP-1 transcriptional cassette contains three copies of a transcriptional activating nucleotide sequence derived from the *Agrobacterium tume- faciens* octopine synthase and, an additional transcriptional activating nucleotide sequence derived from the *Agrobac- terium tumefaciens* mannopine synthase gene, a promoter region derived from the *Agrobacterium tumefaciens* man- nopine synthase gene, a polylinker site for insertion of the nucleotide sequence encoding the polypeptide of interest, and a termination sequence derived from the *Agrobacterium tumefaciens* nopaline synthase gene. The pBMSP-1 expres- sion vector also contains a nucleotide sequence coding for neomycin phosphotransferase II as a selectable marker. Transcription of the selectable marker sequence is driven by a promoter derived from the *Agrobacterium tumefaciens* nopaline synthase gene.

The expression vector pBMSP-3, also used in some of the following examples, contains the components of the pBMSP-1 expression vector described above and addition- ally contains a nucleotide sequence corresponding to nucle- otides 1222–1775 of the maize alcohol dehydrogenase gene (GenBank Accession Number X04049) inserted between the promoter and the polylinker. This sequence is shown in SEQ ID NO:9.

Expression Constructs for the Production of Human α-2b- Interferon in Duckweed

The following expression constructs were constructed using methods well known in the art. See, for example, Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

TABLE 1

| Construct Name | Expression Vector | Signal Peptide | Interferon-encoding Sequence |
|---|---|---|---|
| IFN01 | pBMSP-1 | None | Non-optimized interferon (SEQ ID NO:10; nucleotides 580–1077 of GenBank Accession |

TABLE 1-continued

| Construct Name | Expression Vector | Signal Peptide | Interferon-encoding Sequence |
|---|---|---|---|
| IFN02 | pBMSP-3 | Non-optimized interferon (SEQ ID NO:11; nucleotides 511–579 of GenBank Accession No. J00207) | Non-optimized interferon (SEQ ID NO:10; nucleotides 580–1077 of GenBank Accession No. J00207) |
| IFN03 | pBMSP-3 | *Arabidopsis thaliana* endochitinase (SEQ ID NO:12; nucleotides 338–399 of GenBank Accession number AB023460 with an additional "A" added to the 3' end of the sequence) | Non-optimized interferon (SEQ ID NO:10; nucleotides 580–1077 of GenBank Accession No. J00207) |
| IFN05 | pBMSP-3 | Modified rice α-amylase* (encoding the amino acid sequence shown in SEQ ID NO:7) | Non-optimized interferon (SEQ ID NO:10; nucleotides 580–1077 of GenBank Accession No. J00207) |
| IFN07 | pBMSP-3 | Wild type rice α-amylase (nucleotides 34–126 of GenBank Accession No. M24286, encoding the amino acid sequence shown in SEQ ID NO:6) | Non-optimized interferon (SEQ ID NO:10; nucleotides 580–1077 of GenBank Accession No. J00207) |
| IFN08 | pBMSP-3 | Optimized wild type rice α-amylase (SEQ ID NO:3) | Non-optimized interferon (SEQ ID NO:10; nucleotides 580–1077 of GenBank Accession No. J00207) |
| IFN09 | pBMSP-3 | Optimized wild type rice α-amylase (SEQ ID NO:3) | Optimized interferon (SEQ ID NO:2) |
| IFN10 | pBMSP-3 | None | Optimized interferon (SEQ ID NO:2) |
| IFN11 | pBMSP-1 | Optimized wild type rice α-amylase (SEQ ID NO:3) | Optimized interferon (SEQ ID NO:2) |
| IFN12 | pBMSP-1 | None | Optimized interferon (SEQ ID NO:2) |

*The nucleotide sequence encoding the modified rice α-amylase signal peptide corresponds to nucleotides 34–126 of GenBank Accession No. M24286, except that nucleotides 97–102 have been changed from "CTTGGC" to "ATCGTC."

Transformation of Duckweed

Duckweed fronds or duckweed nodule cultures (derived from *Lemna minor* strain 8627 in these examples) are transformed with the expression constructs described above using Agrobacteria-mediated transformation methods. *Agrobacterium tumefaciens* strain C58Z707, a disarmed, broad host range C58 strain (Hepburn et al. (1985) *J. Gen. Microbiol.* 131:2961–2969) is used for transformation in these examples. The expression constructs described above are mobilized into *A. tumefaciens* by electroporation, or by a triparental mating procedure using *E. coli* MM294 harboring the mobilizing plasmid pRK2013 (Hoekema et al. (1983) *Nature* 303: 179–180; Ditta et al. (1980) *Proc. Natl. Acad. Sci. USA* 77: 7347–7350). C58Z707 strains comprising the expression constructs described above are streaked on AB minimal medium (Chilton et al., (1974) *Proc. Nat. Acad. Sci. USA* 71: 3672–3676) or in YEB medium (1 g/L yeast extract, 5 g/L beef extract, 5 g/L peptone, 5 g/L sucrose, 0.5 g/L MgSO$_4$) containing streptomycin at 500 mg/L, spectinomycin at 50 mg/L and kanamycin sulfate at 50 mg/L and grown overnight at 28° C.

In these examples, *Lemna minor* strain 8627 is used for transformation although any *Lemna* strain can be used. Fronds are grown on liquid Schenk and Hildebrandt medium (Schenk and Hildebrandt (1972) *Can. J Bot.* 50:199) containing 1% sucrose and 10 µM indoleacetic acid at 23° C. under a 16 hour light/8 hour dark photoperiod with light intensity of approximately 40 µM/m$^2$·sec. For inoculation, individual fronds are separated from clumps and floated in inoculation media for approximately 2 to 20 minutes. The inoculating medium is Schenk and Hildebrandt medium (pH 5.6) supplemented with 0.6 M mannitol and 100 µM acetosyringone, with the appropriate *Agrobacterium tumefaciens* strain comprising the expression construct present at a concentration of about 1×10$^9$cells/ml. These fronds are then transferred to Schenk and Hildebrandt medium (pH 5.6) containing 1% sucrose, 0.9% agar, and 20 mg/L acetosyringone and are co-cultivated for 3 or 4 days in the dark at 23° C.

Following co-cultivation, the fronds are transferred for recovery to Schenk and Hildebrandt medium or Murashige and Skoog medium (Murashige and Skoog (1962) *Physiol. Plant.* 15:473) supplemented with 200 µg/ml kanamycin sulfate. Fronds are decontaminated from infecting Agrobacteria by transferring the infected tissue to fresh medium with antibiotic every 2–4 days. The fronds are incubated on this medium for approximately four weeks under conditions of low light (1–5 µM/ml sec).

Duckweed nodule cultures for transformation are produced as follows. Duckweed fronds are separated, the roots are cut off with a sterile scalpel, and the fronds are placed, ventral side down, on Murashige and Skoog medium (catalog number M-5519; Sigma Chemical Corporation, St. Louis, Mo.) pH 5.6, supplemented with 5 µM 2,4-dichlorophenoxyacetic acid, 0.5 µM 1-Phenyl-3(1,2,3-thiadiazol-5-yl) urea thidiazuron (Sigma P6186), 3% sucrose, 0.4 Difco Bacto-agar (Fisher Scientific), and 0.15% Gelrite (Sigma). Fronds are grown for 5–6 weeks. At this time, the nodules (small, yellowish cell masses) appear, generally from the central part of the ventral side. This nodule tissue is detached from the mother frond and cultured in Murashige and Skoog medium supplemented with 3% sucrose, 0.4% Difco Bacto-agar, 0.15% Gelrite, 1 µM 2,4-dichlorophenoxyacetic acid, and 2 µM benzyladenine.

Duckweed nodule cultures are transformed as follows. The appropriate *Agrobacterium tumefaciens* strain is grown on potato dextrose agar or YEB agar with 50 mg/L kanamycin and 100 μM acetosyringone, and resuspended in Murashige and Skoog medium supplemented with 0.6 M Mannitol and 100 μM acetosyringone. Nodule culture tissue is inoculated by immersing in the solution of resuspended bacteria for 1–2 minutes, blotted to remove excess fluid, and plated on co-cultivation medium consisting of Murashige and Skoog medium supplemented with auxin and cytokinin optimized to promote nodule growth and 100 μM acetosyringone.

For selection, nodule culture tissue is transferred to regeneration medium Murashige and Skoog medium with 3% sucrose, 1 μM 2,4-dichlorophenoxyacetate, 2 μM benzyladenine, 0.4% Difco Bacto-Agar, 0.15% Gelrite 500 mg/L cefotaxime, and 200 mg/L kanamycin sulfate and cultured for approximately four weeks under continuous light (20–40 μm$^2$·sec). The nodule tissue is transferred every 7 days to fresh culture medium. Selection is complete when the nodule tissue shows vigorous growth on the selection agent. In some examples, the transformed duckweed nodule cultures are transferred directly to regeneration medium for selection, instead of undergoing selection in co-cultivation medium.

For regeneration of transformed duckweed, the selected nodule culture is transferred to regeneration medium (0.5× Schenk and Hildebrandt medium supplemented with 1% sucrose and 200 mgs/L kanamycin) to organize and produce plants. The nodule culture is incubated on regeneration medium under full light for approximately 3 weeks, until fronds appear. Fully organized fronds are transferred to liquid Schenk and Hildebrandt medium with 1–3% sucrose and incubated under full light for further clonal proliferation. Detection of Biologically-active Interferon Produced from Duckweed Fronds or Duckweed Nodule Culture Biologically-active interferon is detected by various assays, including a solid phase sandwich immunoassay as described in Staehlin et al. (1981) *Methods Enzymol.* 79:589–594 and Kelder et al. (1986) *Methods Enzymol.* 119:582–587, herein incorporated by reference, and a cytopathic effect inhibition assay (described in Tovey et al. (1978) *Nature* 276:270–272, herein incorporated by reference. Secreted interferon is collected from the duckweed culture medium, while non-secreted interferon is collected from ground-up or lysed duckweed plants or duckweed nodule tissue.

The solid phase sandwich immunoassay for interferon is performed using a kit from PBL Laboratories (New Brunswick, N.J.) according to the manufacturer's instructions. Briefly, interferon is captured by an antibody bound to the microtiter plate wells. A second antibody is then used to reveal the bound antibody. An anti-secondary antibody conjugated to horseradish peroxidase (HRP) is then used to mark the interferon. Tetramethyl benzidine (TMB) initiates a peroxidase-catalyzed color change so that the interferon level can be observed and compared with a standard. A monoclonal antibody specific for α-2b-interferon (Cat. No. 11105, PBL Laboratories) is used for this assay in the present examples.

The cytopathic effect inhibition assay is performed according to the methods of Tovey et al. (1978) *Nature* 276:270–272. Briefly, serial two-fold dilutions of the preparation to be assayed are diluted in a 96 well microtiter plate (Falcon Inc) in a volume of 100 μl of Eagles minimal essential medium (Life Technologies Inc) supplemented with 2% fetal calf serum (Life Technologies Inc) in parallel with serial two fold dilutions of the US National Institutes of Health human IFN alpha international reference preparation (G-002-901-527). Twenty thousand human amnion cells (line WISH) are then added to each well of the microtiter plate in a volume of 100 μl of medium with 2% fetal calf serum. The cells are incubated over-night in an atmosphere of 5% $CO_2$ in air at 37° C., the medium is removed and replaced with 200 μl of medium with 2% fetal calf serum containing vesicular stomatitis virus at a multiplicity of infection of 0.1. The cells are further incubated over-night in an atmosphere of 5% $CO_2$ in air at 37° C. and the cytopathic effect due to virus replication is then evaluated under a light microscope. Interferons titers are expressed as the reciprocal of the IFN dilution which gave 50% protection against the cytopathic effects of the virus. Interferon titers are expressed in international reference units by reference to the titer of the reference preparation.

The following examples demonstrate the expression of biologically active interferon in duckweed.

EXAMPLE 1

Figure 1:
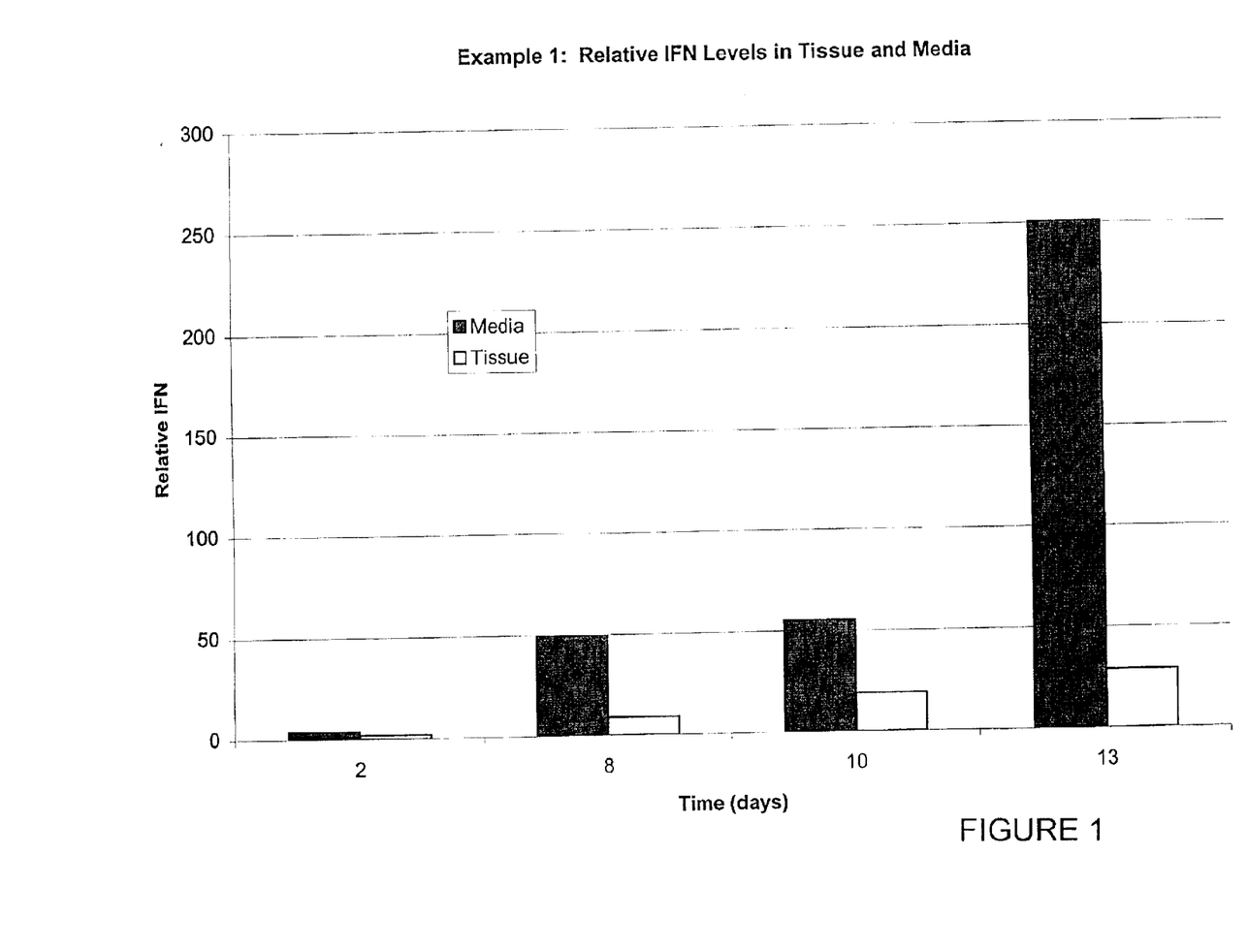
FIG. 1 show the interferon levels (as determined by a solid phase sandwich immunoassay) in the media and tissue of a transformed duckweed culture, as described Example 1.

A study was performed to determine culture IFN levels in media and tissue at various time points in a batch culture. A set of 20–30 ml 175 oz.-culture jars were inoculated on Day 0 with 20 fronds of a line previously identified as expressing detectable levels of human α-2b-interferon (IFN). The cultures were grown under autotrophic, buffered conditions with continuous high light provided by plant/aquarium fluorescent grow bulbs. At each time point—days 5, 7, 13, 15, and 18—the fresh weight and media volume were measured for four cultures. From each culture, media and tissue samples were obtained and a plant protease inhibitor cocktail was added. The tissue samples were ground and spun cold. The supernatant was collected. Media and tissue extracts were stored at −70° C. until all samples were collected. IFN levels in media and tissue extracts were determined on the same day using the solid phase sandwich immunoassay described above. Total culture IFN in media and tissue was calculated by multiplying measured IFN concentrations and the volume of media and the fresh weight for the culture, respectively. FIG. 1 shows the relative IFN levels on days 7, 13, 15, and 18 compared to day 5. The last time point represents the average value for three cultures instead of four due to loss of one culture.

EXAMPLE 2

Figure 2:
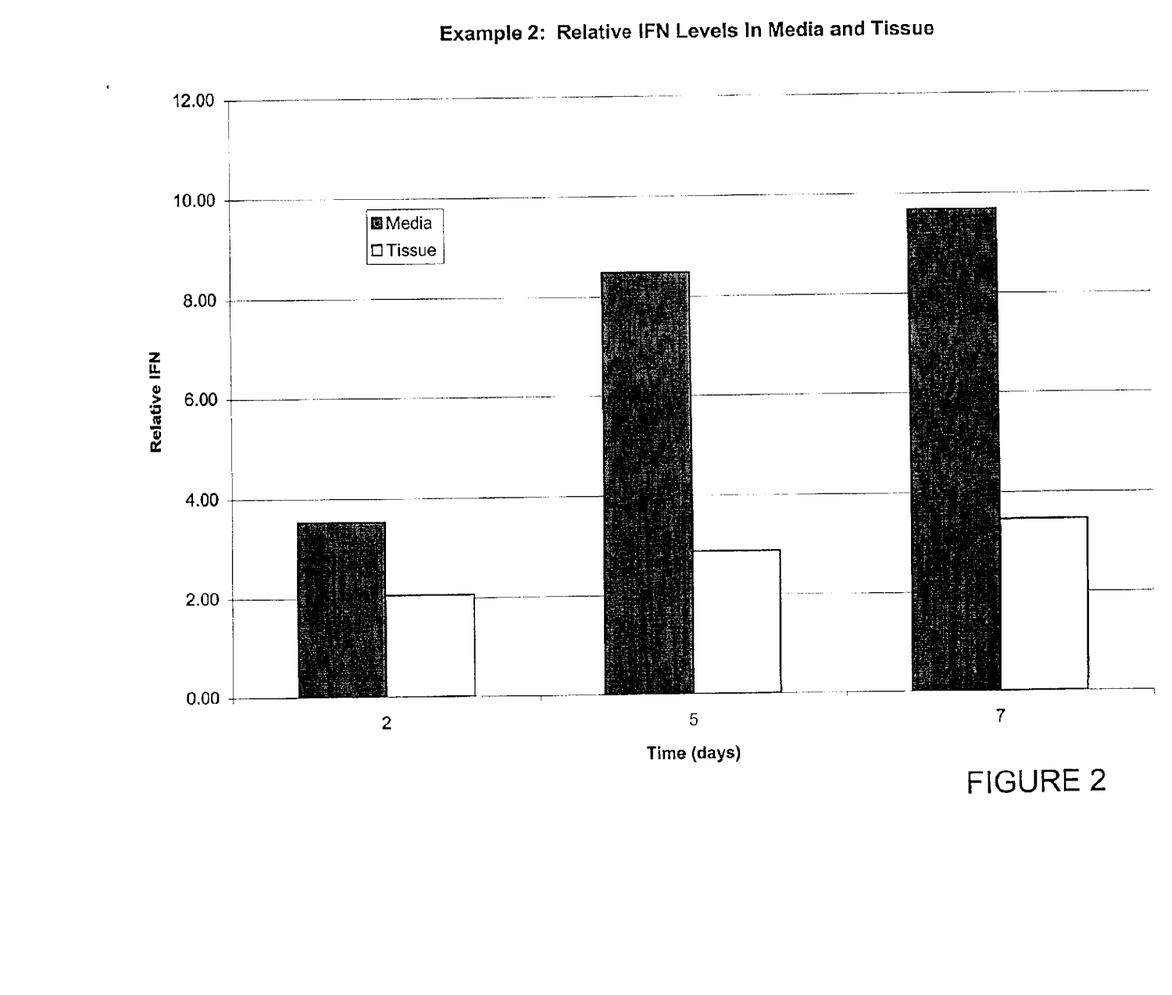
FIG. 2 show the interferon levels (as determined by a solid phase sandwich immunoassay) in the media and tissue of a transformed duckweed cultures, as described in Example 2.

A study was performed to determine culture IFN levels in media and tissue at various time points in a batch culture. A set of 24–30 ml 175 oz.-culture jars were inoculated on Day 0 with 20 fronds same line as in Example 1. The cultures were grown under autotrophic, unbuffered conditions with continuous high light provided by plant/aquarium fluorescent grow bulbs. At each time point—days 7, 10, 12, 14, 17, and 19—the fresh weight and media volume were measured for four cultures. From each culture, media and tissue samples were obtained and a plant protease inhibitor cocktail was added. The tissue samples were ground and spun cold. The supernatant was collected. Media and tissue extracts were stored at −70° C. until all samples were collected. IFN levels in media and tissue extracts were determined on the same day using the solid phase sandwich immunoassay described above. Total culture IFN in media and tissue was calculated by multiplying measured IFN concentrations and the volume of media and the fresh weight for the culture, respectively. FIG. 2 shows the relative IFN levels on days 14, 17, and 19 compared to day 12. Media IFN levels on day 7 and day 10 were below the range of the extended range protocol for the immunoassay.

EXAMPLE 3

Duckweed lines transformed with the expression constructs listed in Table 1 were produced using the methods described above. These transformed duckweed lines were grown for 14 days under autotrophic conditions. Bovine serum albumin at a concentration of 0.2 mg/ml was included in the growth media. On day 14, media and tissue extracts were prepared as described in Example 1, and the interferon levels in these extracts were determined using the solid phase sandwich immunoassay as described above. Table 2 gives the number of clonal duckweed lines assayed and the mean media interferon concentration for each expression construct. Table 3 shows the interferon levels within the duckweed tissue for the duckweed lines transformed with the interferon expression constructs that did not contain a signal peptide (IFN01, IFN10, and IFN12). Both the mean interferon level for all clonal lines assayed for the designated construct, and the interferon level for the top-expressing line are shown.

TABLE 2

| Expression Construct | # of Clonal Lines Tested | Mean Interferon Concentration (ng/ml) |
|---|---|---|
| IFN01 | 41 | 0 |
| IFN02 | 75 | 2.3 |
| IFN03 | 41 | 0.18 |
| IFN05 | 44 | 2.5 |
| IFN07 | 41 | 1.5 |
| IFN08 | 41 | 1.4 |
| IFN09 | 41 | 30.3 |
| IFN10 | 41 | 0 |
| IFN11 | 39 | 9.9 |
| IFN12 | 41 | 0 |

TABLE 3

| IFN Construct | Mean Value % of total soluble protein | Top Expresser % of total soluble protein |
|---|---|---|
| IFN01 | 0.00003 | 0.0001 |
| IFN10 | 0.00064 | 0.0074 |
| IFN12 | 0.00014 | 0.001 |

The biological activity of the interferon produced by these transformed duckweed lines was assayed by the cytopathic effect inhibition assay described above. Table 4 gives the results for the top expressing line for each construct. The interferon activity is shown for the media for those constructs containing a signal peptide and the tissue for those constructs lacking a signal peptide.

TABLE 4

| | Top Expresser | |
|---|---|---|
| IFN Construct | Source material | IU/ml (media) IU/mg total protein (tissue) |
| IFN01 | Tissue | 40 |
| IFN02 | Media | 16,000 |
| IFN03 | Media | 320 |
| IFN05 | Media | 6,400 |
| IFN07 | Media | 6,000 |
| IFN08 | Media | 3,200 |
| IFN09 | Media | 200,000 |
| IFN10 | Tissue | 19,300 |
| IFN11 | Media | 30,000 |
| IFN12 | Tissue | 150 |

The following features can be noted for the data in this example: (1) Secretion of interferon was detected only for those duckweed lines transformed with expression constructs containing a signal peptide. Compare, for example, the media interferon concentration for IFN02, IFN03, IFN05, IFN07, IFN08, IFN 09 and IFN011 with that for IFN01, IFN10, and IFN12. (2) Secretion of interferon was detected for all expression constructs containing a signal peptide, with the native human interferon signal sequence producing the highest level of secreted interferon. Compare, for example, the interferon levels produced by IFN02 with those produced by IFN03 and IFN05. (3) The use of duckweed-preferred codons leads to enhanced interferon expression. Compare, for example, the interferon levels produced by IFN09 with those for IFN05. (4) Higher expression levels were achieved by the codon optimization of more than just the signal peptide. Compare, for example, IFN08 with IFN09. (5) Including the maize alcohol dehydrogenase intron sequence in the expression construct resulted in higher levels of interferon expression. Compare, for example, IFN09 with IFN11 and IFN10 with IFN12. (6) No statistically significant difference was observed between the interferon levels expressed from the construct containing the modified α-amylase signal peptide (IFN05) in comparison with that containing the wild-type alpha amylase signal peptide (IFN07).

TABLE 5

| Lemna gibba-preferred codons from GenBank Release 113 | | | | | | | |
|---|---|---|---|---|---|---|---|
| UUU 2.2 | ( 4) | UCU 0.5 | ( 1) | UAU 2.2 | ( 4) | UGU 0.0 | ( 0) |
| UUC 50.5 | ( 92) | UCC 31.9 | ( 58) | UAC 40.4 | ( 73) | UGC 17.6 | ( 32) |
| UUA 0.0 | ( 0) | UCA 0.5 | ( 1) | UAA 3.8 | ( 7) | UGA 1.6 | ( 3) |
| UUG 2.7 | ( 5) | UCG 15.4 | ( 28) | UAG 0.0 | ( 0) | UGG 24.2 | ( 44) |
| CUU 0.5 | ( 1) | CCU 6.6 | ( 12) | CAU 0.5 | ( 1) | CGU 1.1 | ( 2) |
| CUC 39.0 | ( 71) | CCC 43.4 | ( 79) | CAC 6.6 | ( 12) | CGC 26.9 | ( 49) |
| CUA 1.1 | ( 2) | CCA 2.2 | ( 4) | CAA 4.4 | ( 8) | CGA 1.1 | ( 2) |
| CUG 22.5 | ( 41) | CCG 20.9 | ( 38) | CAG 26.9 | ( 49) | CGG 7.7 | ( 14) |
| AUU 0.0 | ( 0) | ACU 3.3 | ( 6) | AAU 1.1 | ( 2) | AGU 0.0 | ( 0) |
| AUC 33.5 | ( 61) | ACC 26.4 | ( 48) | AAC 37.9 | ( 69) | AGC 22.0 | ( 40) |

TABLE 5-continued

Lemna gibba-preferred codons from GenBank Release 113

| | | | | | | | | |
|---|---|---|---|---|---|---|---|---|
| AUA 0.0 | ( 0) | ACA 0.5 | ( 1) | AAA 0.0 | ( 0) | AGA 4.9 | ( 9) |
| AUG 33.5 | ( 61) | ACG 9.3 | ( 17) | AAG 87.1 | ( 104) | AGG 6.0 | ( 11) |
| GUU 9.3 | ( 10) | GCU 7.1 | ( 13) | GAU 1.6 | ( 3) | GGU 1.1 | ( 2) |
| GUC 28.0 | ( 51) | GCC 73.6 | ( 134) | GAC 38.4 | ( 70) | GGC 46.7 | ( 85) |
| GUA 0.0 | ( 0) | GCA 5.5 | ( 10) | GAA 2.2 | ( 4) | GGA 1.1 | ( 2) |
| GUG 34.0 | ( 62) | GGG 20.9 | ( 38) | GAG 62.6 | ( 114) | GGG 27.5 | ( 50) |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of producing biologically active α-2b-interferon in a duckweed plant culture or a duckweed nodule culture, comprising the steps of:
   (a) culturing within a duckweed culture medium a duckweed plant culture or a duckweed nodule culture, wherein said duckweed plant culture or said duckweed nodule culture is stably transformed to express said biologically active α-2b-interferon, and wherein said biologically active α-2b-interferon is expressed from a nucleotide sequence comprising a coding sequence for the polypeptide and an operably linked coding sequence for a signal peptide that directs secretion of the α-2b-interferon into the culture medium; and
   (b) collecting said biologically active α-2b interferon from the duckweed culture medium.

2. The method of claim 1, wherein said biologically active α-2b-interferon is secreted into the duckweed culture medium.

3. The method of claim 1, wherein said nucleotide sequence has at least one attribute selected from the group consisting of:
   (a) duckweed-preferred codons in the coding sequence for said α-2b-interferon;
   (b) duckweed-preferred codons in the coding sequence for said signal peptide;
   (c) a translation initiation codon that is flanked by a plant-preferred translation initiation context nucleotide sequence, wherein said plant-preferred translation initiation context nucleotide sequence consists of the nucleotide sequence "ACC" or "ACA", wherein said context is positioned immediately adjacent to of the 5' end of the translation initiation codon; and
   (d) an operably linked nucleotide sequence comprising a plant intron that is inserted upstream of the coding sequence.

4. The method according to claim 3, wherein said duckweed-preferred codons are *Lemna gibba*-preferred codons or *Lemna minor*-preferred codons.

5. The method according to claim 4, wherein at least one coding sequence selected from the coding sequence for said polypeptide and the coding sequence for said signal peptide comprises between 70–100% *Lemna gibba*-preferred codons or *Lemna minor*-preferred codons.

6. The method according to claim 3, wherein said operably linked nucleotide sequence comprising said plant intron is the sequence set forth in SEQ ID NO:1.

7. A method of producing biologically active α-2b-interferon, comprising the steps of:
   (a) culturing a duckweed plant culture or a duckweed nodule culture, wherein said duckweed plant culture or said duckweed nodule culture is stably transformed to express said biologically active α-2b-interferon, and wherein said biologically active α-2b-interferon is encoded by a nucleotide sequence that has been modified for enhanced expression in duckweed, and
   (b) collecting said biologically active α-2b-interferon from said duckweed plant culture or said duckweed nodule culture.

8. The method of claim 7, wherein said nucleotide sequence that has been modified for enhanced expression in duckweed has at least one attribute selected from the group consisting of:
   (a) duckweed-preferred codons in the coding sequence for said biologically active α-2b-interferon;
   (b) a translation initiation codon that is flanked by a plant-preferred translation initiation context nucleotide sequence, wherein said plant-preferred translation initiation context nucleotide sequence consists of the nucleotide sequence "ACC" or "ACA", wherein said context is positioned immediately adjacent to the 5' end of the translation initiation codon; and (c) an operably linked nucleotide sequence comprising a plant intron that is inserted upstream of the coding sequence.

9. The method according to claim 8, wherein said duckweed-preferred codons are *Lemna gibba*-preferred codons or *Lemna minor*-preferred codons.

10. The method according to claim 9, wherein the coding sequence comprises betwee 70% and 100% *Lemna gibba*-preferred codons or *Lemna minor*-preferred codons.

11. The method according to claim 8, wherein said operably linked nucleotide sequence comprising said plant intron is the sequence set forth in SEQ ID NO:1.

12. The method according to claim 1, wherein said α-2b-interferon is a human α-2b-interferon.

13. The method according to claim 12, wherein said human α-2b-interferon has an amino acid sequence selected from the group consisting of the amino acid sequence set forth in SEQ ID NO:4 and the amino acid sequence set forth in SEQ ID NO:5.

14. The method according to claim 1, wherein the biologically active α-2b-interferon variant having at least 80% sequence identity with an amino acid sequence selected from the group consisting of the amino acid sequence set forth in SEQ ID NO:4 and the amino acid sequence set forth in SEQ ID NO:5.

15. The method according to claim 1, wherein said signal peptide is selected from the group consisting of:
  (a) the human α-2b-interferon signal peptide,
  (b) the *Arabidopsis thaliana* chitinase signal peptide;
  (c) the rice α-amylase signal peptide;
  (d) the modified rice α-amylase peptide;
  (e) a duckweed signal peptide; and
  (f) a signal peptide native to the biologically active recombinant polypeptide.

16. The method according to claim 15, wherein the signal peptide is the rice α-amylase signal peptide having the sequence set forth in SEQ ID NO:3.

17. The stably transformed duckweed plant culture or duckweed nodule culture according claim 1.

* * * * *